US00PP22898P3

(12) United States Plant Patent
Hamel

(10) Patent No.: US PP22,898 P3
(45) Date of Patent: Jul. 31, 2012

(54) ***ABIES* PLANT NAMED 'BERNADINE GOLD'**

(50) Latin Name: *Abies balsamea*
Varietal Denomination: Bernadine Gold

(76) Inventor: Leo Hamel, Sawyerville (CA)

( * ) Notice: Subject to any disclaimer, the term of this patent is extended or adjusted under 35 U.S.C. 154(b) by 0 days.

(21) Appl. No.: 13/066,224

(22) Filed: Apr. 7, 2011

(65) Prior Publication Data

US 2011/0197325 P1 Aug. 11, 2011

(51) Int. Cl.
*A01H 7/00* (2006.01)

(52) U.S. Cl. ..... Plt./213

(58) Field of Classification Search ..... Plt./213
See application file for complete search history.

(56) References Cited

OTHER PUBLICATIONS

Pluto UPOV-ROM Plant Variety Database, PBR 08-6357, Citation for *Abies* Bernadine Gold 2011/06, one page.*

* cited by examiner

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Abies* cultivar named 'Bernadine Gold' is disclosed, characterized by its pale yellow new foliage and dark green foliage in the Fall. Plants have a distinctive weak curvature to the needles. The new cultivar is an *Abies*, typically suited for ornamental use.

2 Drawing Sheets

Latin name of the genus and species: *Abies balsamea.*
Variety denomination: 'Bernadine Gold'.

BACKGROUND OF THE INVENTION

The new cultivar is the result of a chance discovery in an existing population of *Abies balsamea* plants used for commercial Christmas tree production. The new variety originated as a naturally occurring, whole plant mutation of the unpatented parent variety, *Abies balsamea*. The new variety was first observed by the inventor, Leo Hamel, a citizen of Canada in 1988 in a stand of *Abies balasamea* under cultivation for production of commercial Christmas trees. This stand of trees was originally planted in 1985, and is located in Sawyerville, Quebec Canada. All trees were maintained according to standard Christmas tree industry conditions, including an annual shearing, and normal fertilizer rates.

After several years observing the unique pale yellow new growth consistently on one tree, the inventor selected the new cultivar for asexual reproduction, and first propagated the new variety in late March 2006. Propagation was by vegetative cuttings, grafted onto standard seedlings of *Abies balsamea*, performed at a commercial nursery in Sainte-Christine, Quebec, Canada. 'Bernadine Gold' has since produced additional generations and has shown that the unique features of this cultivar are stable and reproduced true to type. An application for Plant Breeder's Rights was filed in Canada in May of 2008, and granted in 2010. At the time of filing this US plant patent application, April 2011, plants have never been made commercially or publicly available anywhere in the world, and have always been maintained in a restricted environment.

SUMMARY OF THE INVENTION

The cultivar 'Bernadine Gold' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Bernadine Gold.' These characteristics in combination distinguish 'Bernadine Gold' as a new and distinct *Abies* cultivar:

1. New growth emerges pale yellow, turning slowly green towards late Summer.
2. Dark green foliage in the Fall.
3. Weak curvature to needles.

PARENTAL COMPARISON

Plants of the new cultivar 'Bernadine Gold' are similar to the parent *Abies balsamea* in most horticultural characteristics. However, plants of 'Bernadine Gold' differ in producing pale yellow new growth, turning gradually green towards late Summer. Additionally, 'Bernadine Gold' has darker green foliage in the Fall, than found on *Abies balsamea*, and a weak curvature to the needles, whereas *Abies balsamea* has either very weak, or no curvature to the needles.

COMMERCIAL COMPARISON

Plants of the new cultivar 'Bernadine Gold' are best compared to the parent variety.

BRIEF DESCRIPTION OF THE PHOTOGRAPHS

Figure 1:
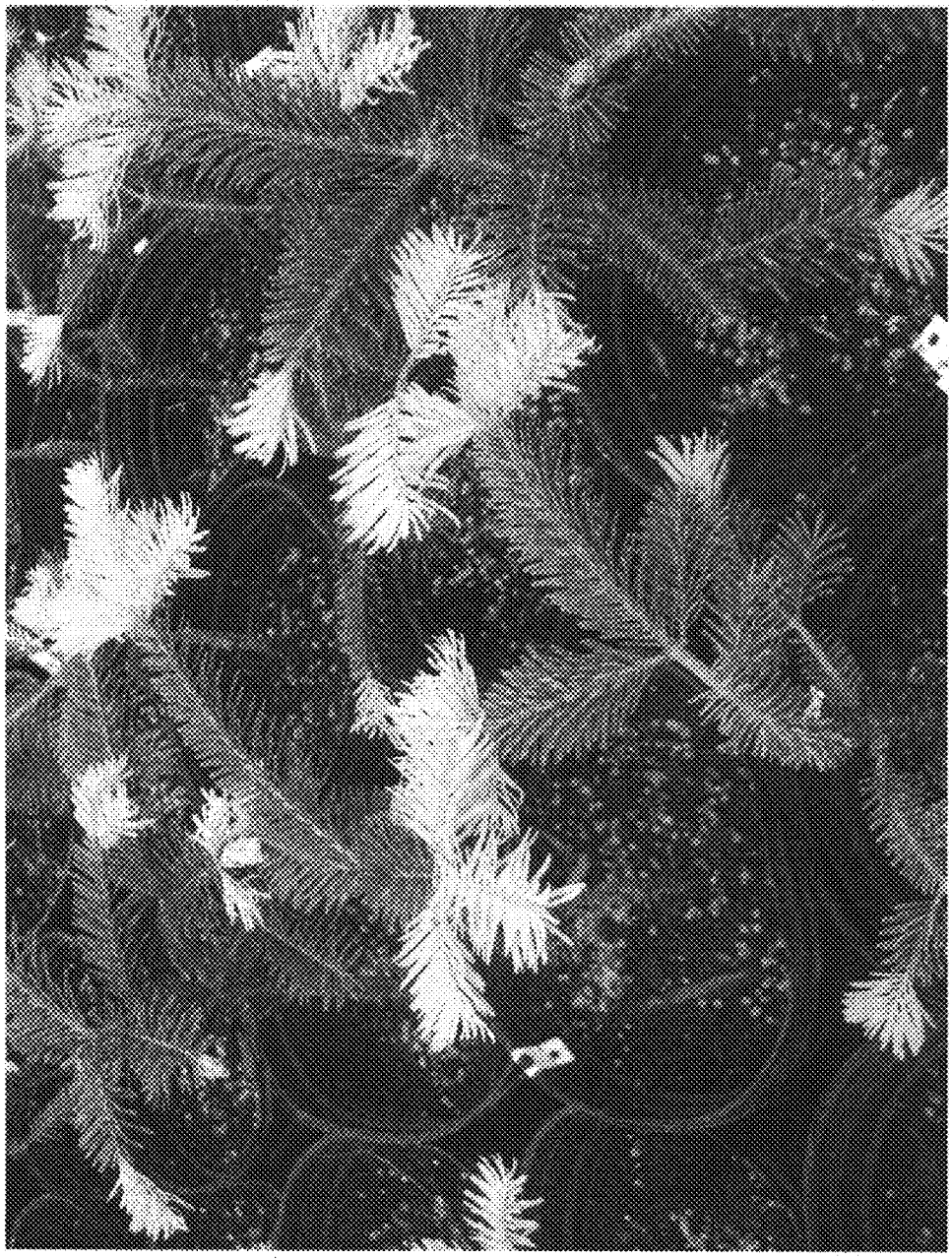

The accompanying photograph in FIG. 1 illustrates in full color a typical plant of 'Bernadine Gold' grown inside an unheated hoop house in Quebec, Canada. This plant is approximately 4 years old, shown in a 3 liter pot.

Figure 2:
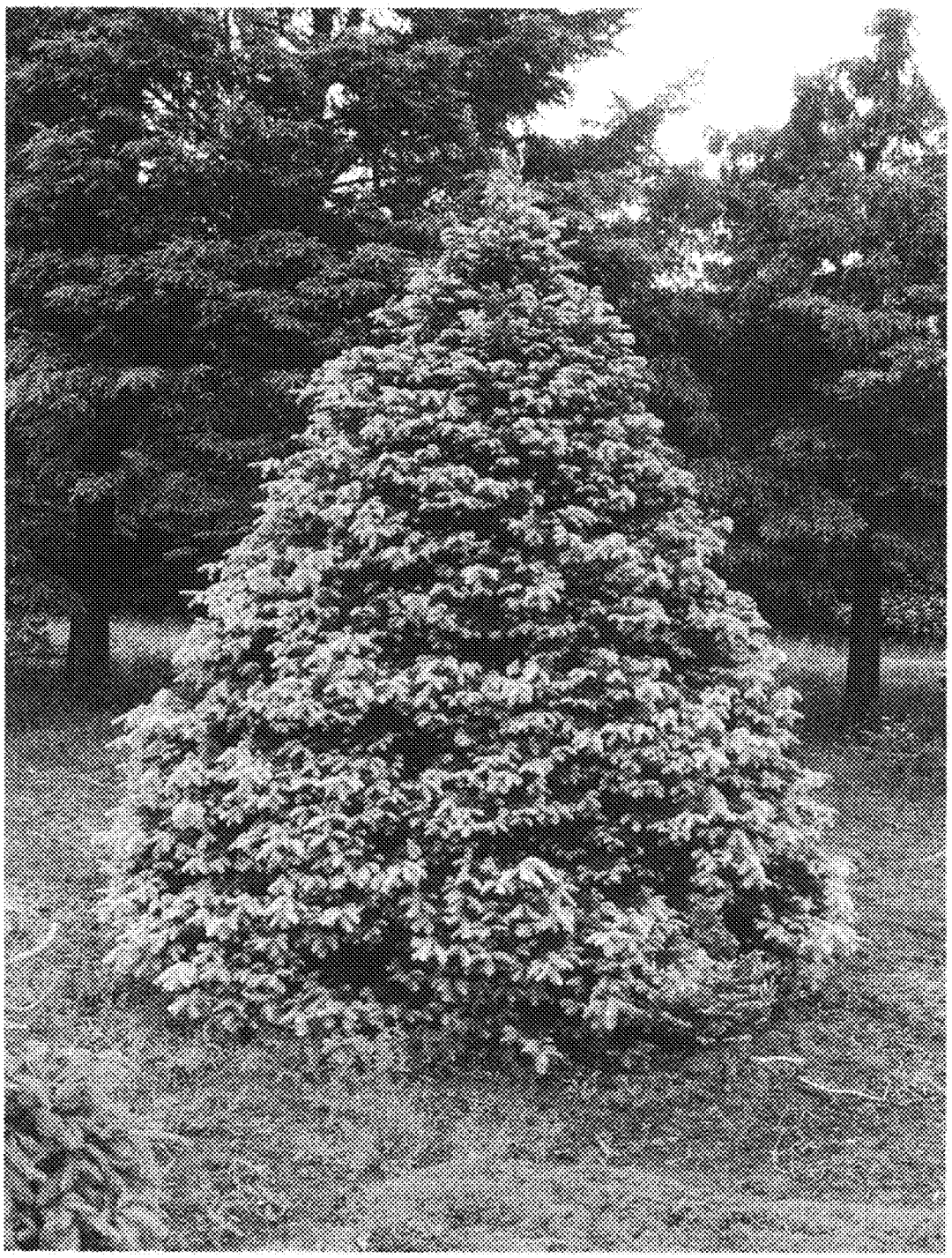

FIG. 2 shows a mature specimen of 'Bernadine Gold' grown outdoors in Quebec Canada. This specimen is approximately 25 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'Bernadine Gold' plants grown outdoors in Sainte-Christine, Quebec, Canada. Unless noted as values taken from a mature plant, values are taken from a plant approximately 4 years old, grown in a 3 liter pot. The plant has been grafted onto a seedling of *Abies balsamea*, and grown in a hoop house for the first 2 years. Temperatures in the hoop house ranged from 15° C. to 25° C. day. From 5° C. to 10° C. night. After the first 2 years in the greenhouse, plants have been grown outdoors in Quebec, Canada. The mature specimen is approximately 25 years old, grown outdoors in Quebec, Canada, given standard commercial Christmas tree production treatment, including an annual shearing. No artificial light, photoperiodic treatments or chemical treatments were given to the plants. Measurements and numerical values represent averages of typical plant types.

Botanical classification: *Abies balsamea* 'Bernadine Gold'.

Age of the plant described: Values are taken from a 4 years old specimen, unless noted as a mature tree measurement.

Container size of the plant described: 3 liter commercial container.

PROPAGATION

Plants are grafted, roots of new variety not observed.

PLANT

Growth habit: Tall pyramidal.

Height: Mature trees are approximately 50-60'.

Plant spread: Mature trees are approximately 20-30'.

Overall plant shape: Conical.

Growth rate: Slow-medium.

Trunk color: Near RHS Grey-Brown 199B.

Trunk diameter: 60 cm, mature tree. Measurement from approximately 20 cm from ground level.

Trunk texture: Smooth.

Branching characteristics:

Diameter of lateral branches: Approximately 1.5-2 cm.

Average length of lateral branches: Approximately 100 to 200 cm.

Quantity of lateral branches: From trunk approx. 4-8 branches per foot of stem. Each of these 4 to 8 branches has a range between 25 to 40 small sub-branches.

Texture of lateral branches: Smooth.

Color of lateral branches: Near RHS Brown N200B.

Aspect and angle: Straight, occurring at approx. 15°-45° from stem.

Strength of lateral branches: Moderate.

Internode length: Approximately 10-15 cm.

Other branch characteristics: Typical of species, blisters of resin, of moderate amount present.

FOLIAGE

Leaf:

*Leaf*.—Arrangement: 2 or more horizontal rows.

*Individual needles*.—Average Length: Approximately 1.5-2 cm. Average Width: Approximately 2-3 mm. Shape of blade: flat narrow needle. Apex: slightly notched to pointed. Base: resembles small suction cup. Attachment: single. Margin: entire. Texture of top surface: smooth. Texture of bottom surface: smooth. Leaf internode length: 1-2 mm. Color: Young foliage upper side: Near RHS Yellow 2D. Young foliage under side: Near RHS Yellow 4A. Mature foliage upper side: Near RHS Green 137C. Mature foliage under side: Near RHS Green 137C.

*Venation*.—Type: parallel. Venation color: Indistinguishable from foliage color.

*Fragrance*.—Sweet, moderate.

REPRODUCTIVE ORGANS

General description of visible parts: Not observed to date.

OTHER CHARACTERISTICS

Cone description:

*Average length*.—Approximately 5-10 cm.

*Average width*.—Approximately 2-4 cm.

*Shape*.—Cylindrical to conical.

*Color*.—Near RHS Grey-Brown N199B.

*Scales*.—Not visible on the closed cone.

Seeds: Not observed to date.

Drought tolerance and temperature tolerance: Low temperature tolerance to approximately −40° C. Tolerates high temperature to at least 30° C. Moderate drought tolerance.

Disease/pest resistance: Neither extra resistance nor susceptibility to the normal pests and diseases of *Abies* has been observed.

What is claimed is:

1. A new and distinct cultivar of *Abies balsamea* plant named 'Bernadine Gold' as herein illustrated and described.

* * * * *